United States Patent [19]

Nowinski et al.

[11] Patent Number: 5,514,542

[45] Date of Patent: May 7, 1996

[54] METHODS FOR PROPAGATING RETROVIRUS FOR USE IN ANTIBODY ASSAYS

[75] Inventors: Robert C. Nowinski, Edmonds, Wash.; Luc Montagnier, Le Plessis-Robinson; David Klatzmann, Paris, both of France

[73] Assignees: Genetic Systems Corporation, Seattle, Wash.; Institut Pasteur, Paris, France

[21] Appl. No.: 406,826

[22] Filed: Mar. 20, 1995

Related U.S. Application Data

[63] Continuation of Ser. No. 774,965, Sep. 27, 1991, abandoned, which is a continuation of Ser. No. 617,466, Nov. 19, 1990, abandoned, which is a continuation of Ser. No. 267,656, Nov. 3, 1988, which is a continuation of Ser. No. 775,842, Sep. 13, 1985.

[51] Int. Cl.⁶ .......................... G01N 33/531; C12N 5/08
[52] U.S. Cl. ..................... 439/5; 435/7.1; 435/7.2; 435/7.9; 435/7.92; 435/235.1; 435/239; 435/240.1; 435/240.2; 435/974
[58] Field of Search .................. 435/4, 5, 7.1, 7.2, 435/7.72, 7.9, 7.92, 235.1, 239, 240.1, 240.2, 240.21, 974

[56] References Cited

U.S. PATENT DOCUMENTS

| | | | |
|---|---|---|---|
| 4,520,113 | 5/1985 | Gallo et al. | 436/504 |
| 4,652,599 | 3/1987 | Gallo et al. | 435/239 |
| 4,716,102 | 12/1987 | Levy et al. | 435/243 |
| 4,725,669 | 2/1988 | Essex et al. | 530/322 |
| 4,877,725 | 10/1989 | Neurath et al. | 435/5 |

OTHER PUBLICATIONS

Yoshiyama et al, Jpn J. Cancer Res 77(6):514–516 (1986).
Woods, Vet Microb 7:427–435 (1982).

*Primary Examiner*—Michael P. Woodward
*Assistant Examiner*—Jeffrey Stucker
*Attorney, Agent, or Firm*—Townsend and Townsend and Crew

[57] ABSTRACT

Cell lines which lack human class II histocompatibility antigens are disclosed. The cell lines may be utilized within a method for propagating microorganisms, such as viruses, for determining the presence and/or amount of antibody to a microorganism in a biological fluid, and within a method for producing antibodies to a selected microorganism.

6 Claims, No Drawings

METHODS FOR PROPAGATING RETROVIRUS FOR USE IN ANTIBODY ASSAYS

This is a continuation of application Ser. No. 07/774,965, filed Sep. 27, 1991, now abandoned, which is a continuing application of Ser. No. 07/617,466 filed Nov. 19, 1990, which is a continuation of Ser. No. 07/267,656 filed Nov. 3, 1988, which is a continuation of Ser. No. 06/775,842 filed Sep. 13, 1985.

TECHNICAL FIELD

This invention relates generally to human cell lines suitable for propagation of microorganisms such as viruses, and more particularly, to such cell lines which lack human class II histocompatibility antigens.

BACKGROUND ART

Viruses have been shown to cause a growing number of clinically significant human diseases. These include influenza virus, the herpes viruses (herpes simplex virus type I and type II (HSV-I and -II), cytomegalovirus (CMV), Epstein-Barr virus (EBV), and *Varicella zoster* (VZ)), hepatitis B virus (HBV), adenovirus, rotavirus, respiratory syncytial virus, polio virus, and measles virus.

Human retroviruses are now also known, the first of these having been obtained from a patient with cutaneous T cell lymphoma (Poiesz et al., *PNAS* 77:7415, 1980) and named Human T Cell Leukemia/Lymphoma Virus type I (HTLV I). Subsequently, a second human retrovirus, designated HTLV II, was isolated from a T cell variant of hairy cell leukemia (Kalyanaraman et al. *Science* 218:571, 1982). More recently the etiologic agent of Acquired Immune Deficiency Syndrome (AIDS) has been shown to be a retrovirus, variously designated Lymphadenopathy Associated Virus (LAV; Barr é-Sinoussi et al., *Science* 220:868, 1983), Human T-Cell Lymphotropic Virus III (HTLV III; Popovic et al., *Science* 224,:497, 1984), or AIDS Related Virus (ARV; Levy et al., *Science* 225:840, 1984). There is also evidence that non-A non-B hepatitis (NANB) may be caused by a retrovirus (Seto et al., *Lancet ii*:941, 1984; Iwarson et al., *J. Med. Virol.* 16:37, 1985).

Laboratory diagnosis of a viral infection can involve either detection of the virus itself or its components, or detection of the host's immune response to the virus (serologic detection). Depending upon the nature of the virus, detection of the virus itself or its components, by culture or by direct diagnosis, may be difficult or impossible. For example, although retroviruses cause persistent infections in animals, including man, retroviral antigens are not always readily detectable in the infected animal (Zagury et al., *Science* 226:449, 1984). For such viruses, serologic detection may be preferable to direct detection.

Serologic diagnosis of a viral infection requires a source of viral protein with which patient sera can be reacted to determine the presence or amount of antibody to the viral agent of interest. Typically, the virus is grown in a human cell line from which it can be purified by methods well known in the art. Many viruses, including the Herpes viruses, polio and measles virus, are cultivated in human diploid fibroblast lines, such as MRC5 or W138, (Smith in *Diagnosis of Viral Infection,* Lenette et al., Eds., Baltimore: University Park Press, 1979, pg.33). HTLV-I and -II are cultivated in continuous T cell lines, such as HUT-102 (Gazdan et al., *Blood* 55:409, 1980; Poiesz et al., supra). LAV can be cultivated in B lymphoblastoid cell lines (Montagnier et al., *Science* 225:62, 1984 ) or in certain continuous T cell lines, such as the H9 cell line described by Popovic et al., supra. There have been conflicting reports concerning the ability of CEM cells to be infected by LAV. Barr é-Sinoussi et al. (.supra) were unsuccessful in transmitting LAV to CEM. However, Cheingsong-Popov et al. (*Lancet i*:477, 1984) and Folks et al. (*PNAS* (USA) 82:4539, 1985) have described the infection of CEM or HAT-sensitive CEM derivatives with LAV.

A number of viruses are known to be transmissible through blood products (blood, blood serum, blood plasma and fractions thereof) making it important to screen the blood products to determine if the donor has been exposed to the virus. Screening can take the form of direct antigen detection (HBV/hepatitis), or detection of antibody to the virus (LAV/AIDS). Detection of antibody to the virus can be accomplished in any of several ways, including enzyme-linked immunosorbent assay (ELISA). Individuals whose blood contains antibodies to the viral agent of interest are said to be seropositive. Blood from seropositive donors is eliminated from the blood supply upon detection, thereby helping to prevent the spread of disease.

When ELISA based screening methods are used for the detection of anti-viral antibody, the incidence of false positives can be relatively high. Recent data on the use of ELISA screening assays for the detection of antibodies to LAV suggests that the problem is due, at least in part, to the presence of antibodies in donor blood to human class II histocompatibility antigens. These antibodies react with antigens from the cells (H9) in which the virus was cultivated (Schorr et al., *New. Eng. J. Med.* 313:384, 1985).

The major histocompatibility complex (MHC) in man is denoted HLA and is encoded by a series of linked loci located on the short arm of chromosome 6. Class I HLA antigens are encoded by the HLA-A,B and C loci, while class II antigens are encoded by the HLA-DR, DP and DQ loci. Class I HLA antigens are expressed on virtually all nucleated cells, while class II antigens are found primarily on cells of the immune system. The HLA antigens are highly polymorphic, i.e., there is a large number of alleles at each locus, hence it is not uncommon to encounter antibodies to HLA antigens in the sera of individuals who have been exposed to cells from other individuals, for example, in persons who have been multiply transfused or who have had multiple pregnancies. In fact, sera from such individuals are presently used as sources of antibody for HLA typing purposes.

Due to incidence of false positives in current screening methods, there is a need in the art for cell lines which are suitable for cultivation of human viruses, yet which cell lines do not possess surface antigens which can elicit false positive reactions in serologic assays. The present invention fulfills this need and further provides other related advantages.

DISCLOSURE OF INVENTION

Briefly stated, the present invention discloses a method for propagating microorganisms, such as viruses in cellular hosts, wherein the cellular hosts do not express human class II histocompatibility antigens. The method generally comprises maintaining a viable culture of cells which lack human class II histocompatibility antigens in a nutrient culture medium, inoculating the culture with a virus to which the cells are susceptible, and subsequently propagating the virus in the culture.

Another aspect of the present invention discloses a method for determining the presence and/or amount of antibody to a microorganism in a biological fluid, comprising (a) incubating the biological fluid with microbial protein isolated from a cellular host which lacks human class II histocompatibility antigens, thereby forming a reaction mixture; and (b) analyzing the reaction mixture to determine the presence and/or amount of antibodies.

An additional aspect of the present invention discloses a somewhat similar method for determining the presence of antibodies to a microorganism in a biological fluid, comprising (a) conjugating latex beads to microbial protein isolated from a cellular host which lacks human class II histocompatibility antigens; (b) incubating the biological fluid with the bead/protein conjugate, thereby forming a reaction mixture; and (c) analyzing the reaction mixture to determine the presence of the antibodies.

Yet another aspect of the present invention discloses a method for producing antibodies to a selected microorganism comprising immunizing an animal with a microbial protein purified from a cellular host which lacks human class II histocompatibility antigens.

Other aspects of the invention will become evident upon reference to the following detailed description.

BEST MODE FOR CARRYING OUT THE INVENTION

Prior to setting forth the invention, it may be helpful to an understanding thereof, to set forth definitions of certain terms to be used hereinafter.

Lymphadenopathy Associated Virus (LAV)—A human T lymphotropic retrovirus. For purposes of the present invention, a virus is considered to be the same as, or equivalent to LAV if it substantially fulfills the following criteria:

a) The virus is tropic for T lymphocytes, especially T helper cells (CD4-positive, according to the international nomenclature defined in Bernard et al., Eds., *Leukocyte Typing,* New York: Springer Verlag, 1984 );

b) The virus is cytopathic for infected CD4-positive cells, rather than transforming, as are HTLV I and II;

c) The virus encodes an RNA-dependent DNA polymerase (reverse transcriptase) which is $Mg^{2+}$ dependent (optimum concentration 5 mM, optimum pH 7.8, not inhibitable by actinomycin D) and can employ oligo $(dT)_{12-18}$ as a primer for reverse transcription from its 3'LTR;

d) The virus bands in a sucrose gradient at a density of 1.16;

e) The virus can be labeled with $[^3H]$ uridine;

f) The virus is distinct by immunological and nucleotide sequence criteria from members of the HTLV I/II family of viruses (by this criterion, HTLV-III is not to be considered a member of the HTLV I/II family);

g) The virus is substantially cross-reactive immunologically with proteins encoded by the gag and env regions of LAV; and h) The virus shares substantial nucleotide sequence homology (75–100%, more often 85–100%) and amino acid sequence homology (75–100%, more often 85–100%) with LAV.

Lymphadenopathy Associated Virus (LAY) can be isolated from patients with AIDS or lymphadenopathy syndrome. The lymph nodes of such patients are typically biopsied and placed in culture medium supplemented as necessary to support growth. A mitogen such as phytohemagglutinin (PHA) or a lymphokine such as interleukin-2 (IL-2) can be included. Antiserum to human interferon can also be included. Reverse transcriptase activity typically appears about day 15 of culture, indicating the presence of virus. The virus can be concentrated from the culture supernatant using a non-ionic detergent, followed by banding in a sucrose gradient. These and other methods of purification are well known in the art and are described for example, in Montelaro et al., *J. Virol.* 42:1029, 1982, incorporated herein by reference.

LAV can be propagated in any of a number of ways. It can be cultured in T lymphocytes derived from umbilical cord or peripheral blood, or from bone marrow. Alternatively, it can be propagated in immortalized T cell lines or B cells , see, for example, Popovic et al., supra and Montagnier et al., supra. Growth of the virus is usually monitored by the presence of reverse transcriptase activity. Virus infection can be cytopathic or non-cytopathic. For example, the H9 cell line and the FR8 EBV-transformed B cell lie (Popovic et al., supra; Montagnier et al., supra) are continuous producers of LAV and exhibit minimal viral cytopathic effect (CPE). In contrast, other T cell lines, such as CEM-F described herein, are susceptible to viral CPE and die gradually over a 3- to 5-day period which coincides with maximum RT activity.

The literature contains conflicting reports on the ability of LAV to infect the CEM cell line. This is most likely due to heterogeneity in the CEM line itself, as it is obtained from ATCC (CCRF-CEM). The CCRF-CEM line types as HLA-A1, A9; B40; Cw 3, 7; and DR$^-$ (Folks et al., supra). This line is not clonal, as evidenced by our ability to clone out a variant (CEM-F) having a different HLA type (shown in Table 3 below).

It is likely that within the deposited line, there are variants which are more or less susceptible to virus infection, hence the conflicting literature. To select for such a variant, CCRF-CEM cells were stained with fluoresceinated monoclonal antibody to the CD4 antigen and sorted by flow microfluorimetry according to antigen density. A clonal line, designated CEM-F, was established from the high CD4$^+$ population. The HLA type of this line is shown in Table 3. This line is extremely susceptible to virus infection, but does not produce virus continuously. Rather, it exhibits viral CPE after several days in culture and gradually dies.

When LAV is cultured in a continuous T cell line such as the H9 cell line described by Popovic (supra), HLA-DR4 and DW3 antigens present on the surface of H9 cells co-purify with the virus. Kuhnl et al., (*The Lancet,* May 25, 1985, p. 1222) and Weiss et al., (*The Lancet,* Jul. 20, 1985, p. 157) have shown that HLA-DR4 typing sera react with virus purified from the H9 cell line. Recent data (Schorr, et al., supra) indicate that as many as 77% of blood units which test positive by ELISA for antibody to LAV are in fact negative by the more stringent criterion of Western blot analysis. It is thought that many of these false positives (i.e. , ELISA-positive, Western blot-negative) are due to donor antibodies reacting with HLA-DR4 antigens in the LAV preparations derived from infected H9 cells.

The instant invention discloses cell lines which lack human class II histocompatibility antigens, such as DR4 and DW3, and are thus useful for the cultivation of viruses such as HTLV, LAV and related retroviruses for serologic screening assays. Some representative, CD4-positive cell lines are shown in Table 1. Of these, the lines CEM and CEM-F are particularly preferred for the cultivation of HTLV and LAV viruses.

TABLE 1

CD4-Positive
Continuous T-Cell Lines

| T-Cell Lines | HLA Class II | CD4 | Reference |
| --- | --- | --- | --- |
| CEM | − | + | 1 |
| CEM-F | − | + | — |
| HPB-ALL | − | + | 2 |
| HPB-MLT | − | + | 2 |
| PEER | − | + | 3 |
| JURKAT (JM) | − | + | 4 |
| TALL-1 | − | + | 4 |
| DND-41 | − | + | 2 |
| CHAN | − | + | 2 |

1 Foley et al., Cancer 18:522, 1965.
2 Martin et al., Immunogenetics 15:385, 1982.
3 Ravid et al., Cancer 15:705, 1980.
4 Schneider et al., Cancer 19:621, 1977.

The CEM cell line is deposited with the ATCC under accession number CCL 119. CEM-F is a variant of CEM, which was selected for high expression of CD4 antigen by flow microfluorimetry. CEM-F has been deposited with the ATCC under accession number (number not yet assigned.

Table 2 lists some additional cell lines which also lack class II antigens, but which are CD4-negative. These lines are useful for the cultivation of lymphotropic viruses which do not preferentially infect T helper (CD4-positive) cells.

TABLE 2

CD4-Negative
Continuous T Cell Lines

| T Cell Lines | HLA Class II | CD4 | Reference |
| --- | --- | --- | --- |
| HSB2 | − | − | 1 |
| MOLT-1,2,3,4 | − | − | 2,3 |
| 8402ALL | − | − | 4 |

1 Adams et al., Exp. Cell Res. 62:5, 1970.
2 Minowanda et al., J. Natl. Cancer Inst. 49:891, 1972.
3 Chechik et al., J. Natl. Cancer Inst. 63:609, 1979.
4 Moore et al., In Vitro 8:434, 1973.

The HSB2 cell line has been deposited (ATCC No. CCL 120.1), as have the MOLT-3 and MOLT-4 cell lines (ATCC Nos. CRL 1552 and CRL 1582, respectively).

The phenotypic characteristics of cell lines suitable for use in the methods of this invention can be established in any of several ways. Typically, cell lines are phenotyped using fluorescently labeled antibodies to the cell surface antigens of interest. Antibody binding is visualized either by fluorescence microscopy or by flow microfluorimetry. The latter method is usually preferred since it provides quantitative information on the expression of the particular antigens of interest.

In this way, cell lines can be selected which do not express class II histocompatibility antigens, but which do express other antigens of interest, e.g., the CD4 antigen. It is also considered useful to re-phenotype the cell line after infection with the virus to ensure that expression of undesired antigens has not been induced by the viral agent. This can be accomplished by the same methods as described above.

Alternatively, cell lines lacking class II antigens can be identified by microcytoxicity assay in which complement-mediated lysis of antigen bearing cells is determined.

Numerous antibodies are described in the literature which are of use in determining whether or not a given cell line expresses class II antigens (see Ninth Int'l Histocompatibility Workshop and Conference, Munich, West Germany, May 6–11, 1984, and published in "Histocompatibility Testing," Eds. Albert, Bauer, and Mayr, Springer-Verlag, Berlin, 1984) and references contained therein for examples). Antibodies, either polyclonal or monoclonal, which react with polymorphic determinants on class II antigens can be used. It is preferred, however, to use antibodies which react with framework determinants on class II antigens, since this simplifies analysis.

Microorganisms isolated from Class II negative cell lines, such as viruses isolated from the cell lines described in the tables can be used for a variety of purposes including as immunogens and as antigens in immunoassays. For use as immunogens, the microorganism virus, or their component proteins can be injected into an animal, such as a mouse, rabbit, goat, etc. either in buffered solution or in adjuvant. Alternatively, the viral microbial or proteins can be partially purified, such as by polyacrylamide gel electrophoresis, and the bands of interest excised from the gel, triturated and resuspended in buffer for injection into the host animal. Either polyclonal or monoclonal antibodies can be prepared.

More specifically, monoclonal antibodies can be prepared by: (a) immunizing an animal with a vital protein purified from a cell line which lacks human class II histocompatibility antigens; (b) fusing spleen cells from the immunized animal to myeloma cells to form hybrid cell lines capable of producing monoclonal antibodies to the virus; (c) culturing the hybrid cell lines to produce the monoclonal antibodies; and (d) collecting the antibodies as a product of the hydrid cell lines.

For use as antigens in immunoassays, microorganisms isolated from Class II negative cell lines, such as virus isolated from the cell lines cited in Table 1 can be employed in labeled or unlabeled form. Where the microbial or viral proteins are labeled, the labels can include radioisotopes, fluorophores, enzymes, luminescers or particles. These and other labels are well known in the art and are described, for example, in the following U.S. Pat. Nos. 3,766,162; 3,791,932; 3,817,837; 3,996,345; and 4,233,402. Assays employing the microbial or viral proteins isolated from the cell lines can be heterogenous, i.e., requiring a separation step, or homogenous. If the assay is heterogenous a variety of separation means can be employed, including centrifugation, filtration, chromatography or magnetism.

One preferred assay for the screening of blood products or other physiological fluids for the presence of anti-viral antibodies is an ELISA assay. Typically, a lysate of virus purified from one of the cell lines described in Table 1 is adsorbed to the surface of a microtiter well. Residual protein binding sites on the surface are then blocked with an appropriate agent, such as bovine serum albumin (BSA), heat inactivated normal goat serum (NGS), or BLOTTO (a buffered solution of non-fat dry milk, which also contains a preservative, salts, and an anti-foaming agent). The well is then incubated with a sample suspected of containing specific antibody. The sample can be applied neat, or more often, it can be diluted, usually in a buffered solution which contains a small amount (typically 0.1–5.0% by weight) of proteins such as BSA, NGS or BLOTTO. After incubating for a sufficient length of time to allow specific binding to occur, the well is washed to remove unbound protein, and then incubated with labeled anti-human immunoglobulin (x-HuIg). The label can be chosen from a variety of enzymes, including horseradish peroxidase (HRP), B-galactosidase (B-gal), alkaline phosphatase (AP), and glucose oxidase (GO). Sufficient time is allowed for specific binding to occur, then the well is again washed to remove unbound conjugate, and the substrate for the enzyme is added. Color is allowed to develop and the optical density of the contents of the well is determined visually or instrumentally.

For convenience, reagents for ELISA assays may be provided in the form of kits. These kits can include microtiter plates, to which a viral lysate has been adsorbed; various diluents and buffers; labeled conjugates for the detection of specifically bound antibodies; and other signal generating reagents, such as enzyme substrates, co-factors and chromogens.

To summarize the examples which follow, Example I illustrates the phenotyping of uninfected and LAV-infected CEM-F cells. Example II illustrates the occurrence of a significant number of false positives when blood units are assayed for the presence of antibodies to LAV using a commercially available ELISA assay which employs LAV (HTLV-III) derived from infected H9 cells (which express class II antigens). The specificity of LAV serologic screening assays was dramatically improved when the samples which yielded false positive results above were re-tested using LAV derived from infected CEM-F cells, which do not express class II antigens.

The following examples are offered by way of illustration and not by way of limitation.

EXAMPLE I

AS shown in the following table, after infection of a cell line susceptible to LAV, there was no change in the HLA type.

TABLE 3

| CEM-F | HLA Type | | | | |
|---|---|---|---|---|---|
| | A | B | C | DR | DQ |
| Uninfected | 1,31 | 8,60 | w1,w3 | neg. | neg. |
| Infected | 1,31 | 8,60 | w1,w3 | neg. | neg. |

EXAMPLE II

An ELISA assay for the detection of antibodies to LAV was performed at the Puget Sound Blood Center (PSBC) using a commercially available kit which employs HTLV-III derived from H9 (DR4$^+$) cells (Abbott Laboratories, HTLV-III ELISA) (Table 4). The first 38 repeatably reactive patient sera were retested by ELISA at Abbott Laboratories. Of these 38, 14 continued to be reactive in the ELISA. These 14 were tested by Western-blot analysis and only four were found to be reactive. The four Western-blot reactive samples were judged to be true positives, while the remaining ten where judged to be false positives. These ten samples were retested in an ELISA using as the source of antigen LAV derived from infected CEM-F cells, which are DR4$^-$. All ten samples were negative in this assay.

The ten sera which were positive in the Abbott ELISA but negative in the CEM-F based ELISA were shown to contain antibodies to HLA-DR4 by their ability to induce complement-mediated cytotoxicity of DR4$^+$ cells. Therefore, antibodies to class II antigens in patient sera result in false positives in ELISA assays using virus derived from class II positive cells.

TABLE 4

| PSBC Results | | Abbott Results | |
|---|---|---|---|
| Ratio* | No. of Donors | EIA+ | WB+ |
| 1–2* | 31 | 9 | 0 |
| >2–8 | 5 | 3 | 2 |
| >8 | 2 | 2 | 1 |
| Total: | 38 | 14 | |

*Ratio is calculated by dividing the sample absorbance value by the cutoof. Thus, any value greater than 1.0 is considered positive.

We claim:
1. A method for determining the presence of antibodies to a retrovirus transmissible through blood products in a biological fluid, comprising:
   incubating the biological fluid with a retroviral lysate immunoreactive with said antibodies, which lysate has been isolated from a CD4-positive cellular host CEM-F which does not express human class II histocompatibility antigens and which cellular host is capable of being infected by said retrovirus, thereby forming a reaction mixture; and
   analyzing the reaction mixture to determine the presence of said antibodies to said retrovirus.
2. The method of claim 1 wherein the step of analyzing the reaction mixture comprises contacting the reaction mixture with a labeled specific binding partner for the antibody and detecting said label.
3. The method of claim 2 wherein the specific binding partner is anti-human Ig or protein A.
4. The method of claim 2 wherein the label is selected from the group consisting of radioisotopes, fluorophores, enzymes, luminescers, and particles.
5. The method of claim 1 wherein the virus is LAV.
6. A method for determining the presence of antibodies to a retrovirus in a biological fluid, comprising:
   conjugating latex beads to a retroviral lysate immunoreactive with said antibodies, which lysate has been isolated from a CD4-positive cellular host CEM-F which does not express human class II histocompatibility antigens and which cellular host is capable of being infected by said retrovirus; and
   incubating the biological fluid with the bead/protein conjugate, thereby forming a reaction mixture; and
   analyzing the reaction mixture to determine the presence of said antibodies to said retrovirus.

* * * * *